(12) United States Patent
Zeegers

(10) Patent No.: US 9,445,915 B2
(45) Date of Patent: *Sep. 20, 2016

(54) INTERVERTEBRAL DISC PROSTHESIS

(71) Applicant: LDR Medical, Rosières Près Troyes (FR)

(72) Inventor: M. Willem Zeegers, Pays-Bas (NL)

(73) Assignee: LDR Medical, Sainte-Savine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,696

(22) Filed: Mar. 9, 2015

(65) Prior Publication Data
US 2015/0245918 A1    Sep. 3, 2015

Related U.S. Application Data

(63) Continuation of application No. 13/215,123, filed on Aug. 22, 2011, now Pat. No. 8,974,532, which is a continuation of application No. 12/391,086, filed on Feb. 23, 2009, now Pat. No. 8,002,835, which is a continuation of application No. 11/098,266, filed on Apr. 4, 2005, now Pat. No. 7,494,508.

(30) Foreign Application Priority Data

Apr. 28, 2004  (FR) .................................. 04 04501

(51) Int. Cl.
A61F 2/44 (2006.01)
A61F 2/30 (2006.01)

(52) U.S. Cl.
CPC ............. *A61F 2/442* (2013.01); *A61F 2/4425* (2013.01); *A61F 2002/3039* (2013.01); *A61F 2002/3065* (2013.01); *A61F 2002/30362* (2013.01); *A61F 2002/30563* (2013.01); *A61F 2002/30616* (2013.01); *A61F 2002/30654* (2013.01); *A61F 2002/443* (2013.01); *A61F 2220/0025* (2013.01); *A61F 2220/0033* (2013.01)

(58) Field of Classification Search
CPC ...... A61F 2/44; A61F 2/4405; A61F 2/4425; A61F 2002/44; A61F 2002/442; A61F 2002/4425; A61F 2002/30362; A61F 2002/3039
USPC ..................... 623/17.11–17.16; 606/246–249
See application file for complete search history.

(56) References Cited

U.S. PATENT DOCUMENTS

| 7,494,508 B2 * | 2/2009 | Zeegers | A61F 2/4425 623/17.11 |
| 8,002,835 B2 * | 8/2011 | Zeegers | A61F 2/4425 623/17.15 |
| 8,974,532 B2 * | 3/2015 | Zeegers | A61F 2/4425 623/17.15 |
| 2004/0010316 A1 * | 1/2004 | William | A61F 2/4425 623/17.16 |

(Continued)

(56) References Cited

*Primary Examiner* — Alvin Stewart
(74) *Attorney, Agent, or Firm* — Lauff Law PLLC

(57) ABSTRACT

The present invention relates to an intervertebral disc prosthesis preferably comprising at least three pieces including an upper plate (1), a lower plate (2) and a mobile core (3) at least in relation to the lower plate (2), co-operation means (23, 33) allowing to limit or eliminate the movements of the core (3) in relation to the lower plate (2), in translation and in rotation, respectively, about an axis substantially parallel to the lower plate (2) and about an axis substantially perpendicular to the lower plate (2), at least one part of the surface of at least one plate being concave and complementary with a convex surface (30) of the core (3), with which it is in contact, wherein the tip (31) of the convex surface (30) of the core (3) is off center, in at least one direction, in relation to the center (32) of this convex surface (30).

6 Claims, 3 Drawing Sheets

(56) References Cited

U.S. PATENT DOCUMENTS

| | | | |
|---|---|---|---|
| 2004/0243240 A1* | 12/2004 | Beaurain | A61F 2/4425 623/17.14 |
| 2005/0027363 A1* | 2/2005 | Gordon | A61F 2/442 623/17.13 |
| 2006/0155377 A1* | 7/2006 | Beaurain | A61F 2/442 623/17.15 |
| 2010/0070046 A1* | 3/2010 | Steinberg | A61B 17/1666 623/22.25 |
| 2012/0053693 A1* | 3/2012 | Zeegers | A61F 2/4425 623/17.16 |

* cited by examiner

INTERVERTEBRAL DISC PROSTHESIS

CROSS REFERENCE TO RELATED APPLICATIONS

This application claims priority under 35 U.S.C. 119 to French Patent Application No. 04 04501, filed in FRANCE on Apr. 28, 2004. This application is a continuation of U.S. application Ser. No. 13/215,123 filed on Aug. 22, 2011, and issuing as U.S. Pat. No. 8,974,532 on Mar. 10, 2015, which is a continuation of U.S. application Ser. No. 12/391,086 filed on Feb. 23, 2009, and issuing as U.S. Pat. No. 8,002,835 on Aug. 23, 2011, which is a continuation of U.S. Application Ser. No. 11/098,266 filed on Apr. 4, 2005, and issuing as U.S. Pat. No. 7,494,508 on Feb. 24, 2009. application Nos. 11/098,266, 12/391,086, and 13/215,123 are incorporated herein by reference.

BACKGROUND

The present invention relates to an intervertebral disc prosthesis, intended to be substituted for fibro-cartilaginous discs ensuring a bond between the vertebrae of the spinal column.

Various types of intervertebral disc prostheses are known in the prior art. Numerous prostheses, such as for example in the patent application FR 2 846 550 and WO 02 089 701, are constituted in a lower plate and an upper plate forming a sort of cage around a central core. A part of these prostheses enables the upper plate to swivel in relation to the central core and optionally permits the central core to slide in relation to the lower plate. This sliding of the central core in relation to the lower plate is an essential characteristic, as it must allow spontaneous positioning of the core in the ideal position to absorb constraints imposed on the prosthesis, during movements made by the patient wearing the prosthesis. The displacement of the core, co-operating with at least a plate about an uneven surface, enables an inclination between the plates of the prosthesis which facilitates the mobility of the patient wearing the prosthesis. The displacement of the core also prevents it from creeping when subjected to major constraints.

In this context, it is significant to propose a prosthesis which allows to impose a permanent inclination between the plates and induces, for example, lordosis. Depending on the disorder of the spinal column of the patient wearing the prosthesis, it is sometimes preferable that the prosthesis allows a correction of this disorder. In line with the wishes of the surgeon, the displacement of the core should be restricted in at least one direction. However, when the patient moves, the relative position of the elements of the prosthesis can be modified, within the permitted range of displacement.

One aim of some embodiments of the present invention is to propose an intervertebral disc prosthesis allowing limited movements of the different pieces of the prosthesis between one another and comprising a core used to restrict its displacement in at least one direction.

SUMMARY

An intervertebral disc prosthesis includes at least three pieces including a first plate, a second plate, and a mobile core, at least in rotation, at least in relation to one of the plates, the core having a curved surface in contact with at least a part of a complementary curved surface of the first plate, and a substantially flat surface in contact with at least a part of a substantially flat of the second, male and female co-operation means situated near the periphery of the second plate and of the core allowing, to limit or prevent, the movements in translation of the core in relation to the second plate to along an axis substantially parallel to the substantially flat surfaces, and allowing to limit or prevent the movements in rotation of the core in relation to the second plate, about an axis substantially perpendicular to the substantially flat surfaces, wherein the top of the curved surface of the core is off centre, in at least one direction, in relation to the geometric centre of this curved surface of the core.

According to another embodiment, the rest position of the core, that being when the patient is motionless, is shifted in the opposite direction to that of the off centre of the top of the curved surface of the core, thanks to the fact that the axes of symmetry of the first and second plates are aligned when the plates are anchored on the vertebrae and that the curved surface of the first plate, complementary with the curved surface of the core, induces the aligning of the off-centre top of this curved surface of the core with the axes of symmetry of the plates and therefore a shifting of the core in the opposite direction to that of the off centre of the top of its curved surface, which provokes a bringing together of the co-operation means present on the core and those present on the second plate, this bringing together consequently limits the displacement of the core in the opposite direction to that of the off centre of the top of its curved surface.

According to anothere embodiment, the same plates can be assembled with different cores, the difference between the cores consisting in the position of the top of their curved surface in relation to the centre of this curved surface of the core.

According to another embodiment, the same cores can be assembled with different plates, the difference between the plates consisting in the angle between the median planes representing the upper and lower surfaces of the plates.

According to another embodiment, an angle between the upper surface of the upper plate and the lower surface of the second plate can be imposed either by the fact that the median planes representing the upper and lower surfaces of the second plate and/or the first plate create an angle, or by restricting, thanks to the co-operation means, movements of the core about a position imposing an inclination of at least one of the plates.

According to another embodiment, the same plates can be assembled with cores of different thicknesses and/or sizes.

According to another embodiment, at least the curved surface of the core is a convex upper surface of the core and the curved surface of the first plate is a concave part of the lower surface of the upper plate are plane.

According to another embodiment, the dimensions of each male co-operation means are slightly less than those of each female co-operation means so as to allow slight clearance between the core and the second plate.

According to another embodiment, the dimensions of each male means are substantially the same as those of each female means so as to prevent any clearance between the core and the second plate.

According to another embodiment, the core is made of polyethylene.

According to another embodiment, first and second plates are made of metal.

According to another embodiment, the second plate comprises female means co-operating with male means of the core.

According to another embodiment, the male means of the core are two contact plates situated on the two site edges of the core and the female means of the second plate are four walls situated, in pairs, on each of the two lateral edges of the second plate.

According to another embodiment, the walls forming the female co-operation means of the second plate are curved toward the centre of the prosthesis, so as to cover at least a part of the male means of the core and to prevent it from lifting.

According to another embodiment, the second plate comprises male means co-operating with female means of the core.

According to another embodiment, the male means of the second plate are two contact plates facing one another on two edges of the prosthesis, and the female means of the core are two recesses.

According to another embodiment, the male means of the second plate are two walls facing one another in the vicinity of two edges of the prosthesis, and the female means of the core are recesses.

According to another embodiment, the male means of the second plate are two nibs curved toward the interior of the prosthesis and facing one another on two edges of the prosthesis, and the female means of the core are two recesses.

According to another embodiment, at least one of the nibs is replaced by a contact plate fitted with a bore on which is fixed a lug by way of a pin penetrating the bore.

According to another embodiment, the first plate is bulged on at least a part of its upper surface to adapt to the form of the vertebrae.

BRIEF DESCRIPTION OF THE DRAWINGS

Other features and advantages of the various embodiments are in the description herein below, given in reference to the attached drawings, in which.

DETAILED DESCRIPTION OF PREFERRED EMBODIMENTS

Figure 1A:
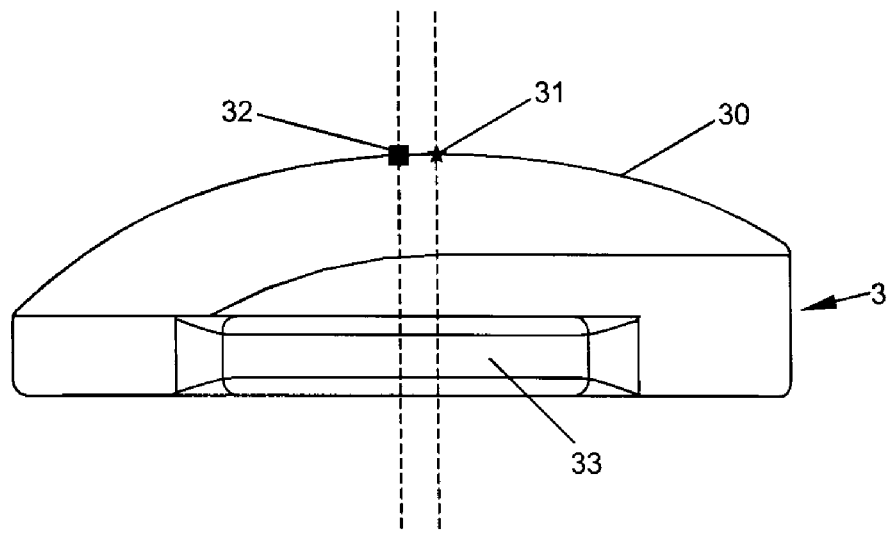
FIGS. 1a and 1b respectively illustrate, a side view and a top view of the core of the prosthesis according to one embodiment of the invention, FIGS. 2a and 2b respectively illustrate a front view and a side view of the prosthesis, in a first embodiment of the invention, and FIGS. 2c and 2d respectively illustrate a front view in perspective and a side view of the prosthesis, in a second embodiment of the invention, FIGS. 3a and 3b respectively illustrate a top view and a cross section view according to the plan A-A in FIG. 3a, of the lower plate of the prosthesis in an embodiment of the invention.

The intervertebral disc prosthesis according to one embodiment of the present invention is constituted in a first plate (1) articulated in relation to a second plate (2) by means of a core (3), as evident in particular in FIGS. 2a to 2d. In the following description, the first plate (1) is called the upper plate and the second plate (2) is called the lower plate, according to the orientation given to the prosthesis shown in the drawings. The prosthesis herein described could also be inversely oriented between the vertebrae, so that the first plate (1) would be the lower plate and the second plate (2) would be the upper plate. As described below, the first plate comprises a curved surface (concave or convex) cooperating with a curved and complementary surface (convex or concave) of the nucleus and the second plate comprises a substantially flat surface cooperating with a substantially flat surface of the nucleus. These various surfaces described can belong to any of the first and second plate of the prosthesis without departing from the scope of the invention.

An advantage of the prosthesis according to this embodiment of the present invention is that it comprises simple pieces which can be dimensioned in order to be adapted to the different vertebrae of the spinal column.

The core (3) is of slight thickness (from 3 to 15 mm, depending on the vertebrae between which the prosthesis is to be inserted). For good absorption of the constraints, the core (3) could, for example, be made of polyethylene, a compressible material simulating the physical properties of elasticity of natural intervertebral discs.

The core (3) preferably has a convex part (30) on at least a part of at least one of its upper and lower surfaces. Preferably, the core (3) also has male or female co-operation means (33) complementary with respectively female or male co-operation means (23) present on at least one of the plates (1, 2).

The description of one of these embodiments will now be dealt with in reference to FIGS. 1 to 3. In this embodiment, it is the upper surface of the core (3) which has a convex part (30), evident particularly in FIG. 1a. This convex surface (30) of the core (3) is complementary with a concave part (10) of the upper plate (1), evident particularly in FIGS. 3d and 3e. This concave part (10) allows to incline the upper plate (1) when the patient wearing the prosthesis bends over. The lower surface of the core (3) and the upper surface of the lower plate (2) could be plane so as to permit clearance of the core (3) in relation to the lower plate (2), both in translation according to an axis substantially parallel to the lower plate (2), and in rotation about an axis substantially perpendicular to the lower plate (2). During movements by the patient wearing the prosthesis, this inclination of the upper plate (1) and this clearance of the core will allow displacement of the core (3) towards the ideal position to absorb the constraints applied to the prosthesis. The movement between the upper plate (1) and the core (3), as well as the clearance of the core (3) in relation to the lower plate (2) thus allow the patient to move, and, optionally, to eliminate the defects of positioning the prosthesis. This clearance likewise has the advantage of preventing premature wear due to the constraints applied to the prosthesis.

Figure 2A:
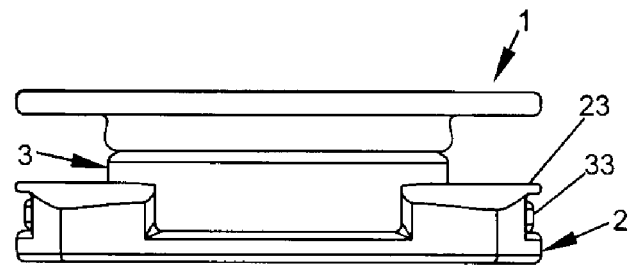
Figure 2B:
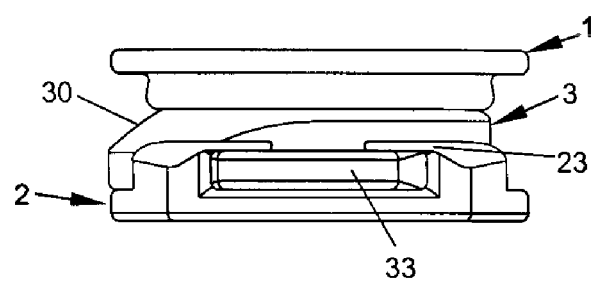
Figure 2C:
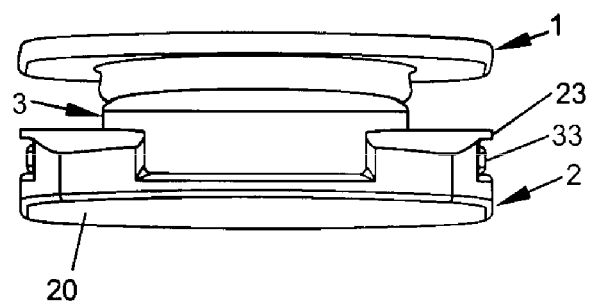
Figure 2D:
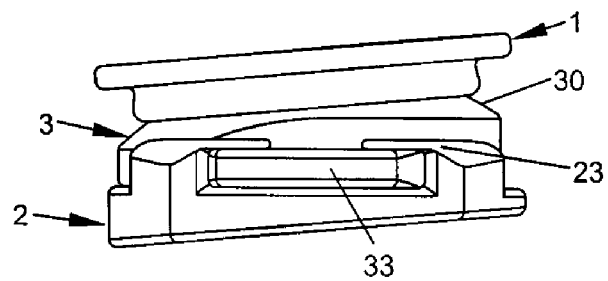

The intervertebral disc prosthesis according to some embodiments allows, for example, to correct the defects of lordosis. The presence of an angle between the upper plate (1) and the lower plate (2) of the prosthesis could be desirable. Such an angle could be obtained by making an upper plate, whose median planes representing its lower and upper surfaces create an angle. Another possibility involves the lower plate whereof the median planes representing its lower and upper surfaces create an angle, as illustrated in FIGS. 2c and 2d, in which the lower surface (20) of the lower plate (2) create an angle with its upper surface. Another possibility to obtain such an angle is only allowed by prostheses of the same type as those of preferred embodiments of the invention and consists in a slightly offset position of the core in relation to the centre of the prosthesis. This slightly offset position of the core can, for example, be maintained thanks to an adjustable positioning of the male and female co-operation means between themselves. If the surgeon wishes, for example, that the prosthesis induces lordosis which remains within a range of values, he will select a prosthesis whose core (3) can have slight clearance in translation and in rotation in relation to the lower plate (2), but about a position imposing a slight permanent inclination of at least one of the plates, thanks to an accurate adjustment of the co-operation means between the core and the lower plate (2).

Figure 3A:
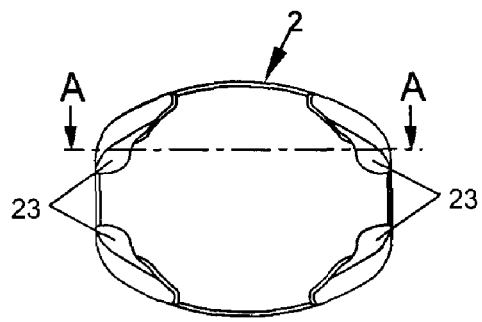
FIG. 3c illustrates a top view of the lower plate with the core and FIGS. 3d and 3e respectively illustrate a top view and a cross section view according to the plan B-B in FIG. 3d, of the upper plate of the prosthesis in an embodiment of the invention.
Figure 3B:
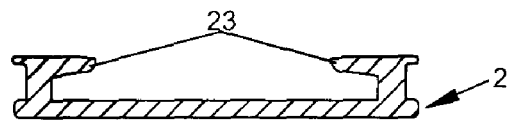
Figure 3C:
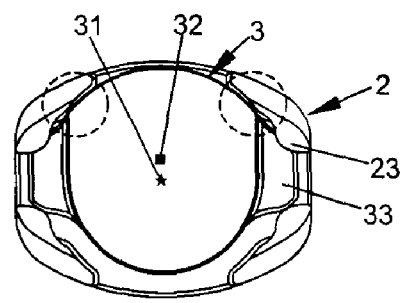
Figure 3D:
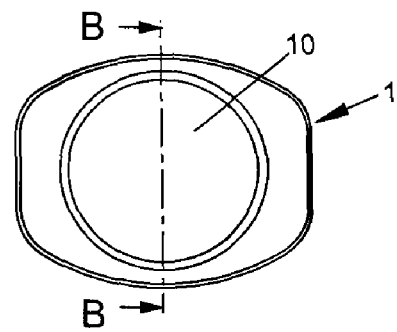
Figure 3E:
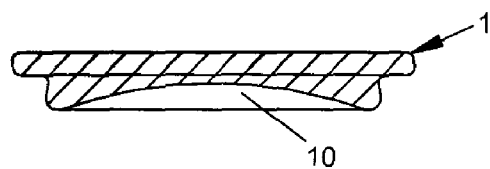

The prosthesis according to preferred embodiments has a characteristic which improves its behaviour once positioned between the vertebrae of the patient. This feature resides in the fact that the top (31) of the curved surface (30) of the core (3), i.e. the highest point (31) of this curved surface (in a side view), is off centre in relation to the geometric_centre (32) of this curved surface (30) of the core (3), i.e. the point (32) equidistant from any point in the periphery of the curved surface (in a top view) or the intersection of the longitudinal and the transversal axes of symmetry of the core (3). In the examples shown, the curved surface (30) of the core (3) is convex and the curved surface of the first plate is a concave part (10) of the lower surface of the upper plate (1), but the various elements of the instant prosthesis can be rearranged so that the convex surface is on one of the plates and the concave surface is on the core. The centre of the concave part (10) of the upper plate (1), complementary with this convex surface (30), swivels around this top (31) of the convex surface (30). Although being mobile about this top (31), the upper plate (1) will therefore be on average centred on the top (31) of the convex surface (30) of the core (3). The vertical axes which pass through the centres of two adjacent vertebrae are generally aligned, even though they can be slightly inclined depending on the movements of the patient or depending on the zone in question of the spinal column. It is therefore important that the vertical axes which pass through the centres of the plates (1, 2) and through the top (31) of the convex surface (30) of the core are also aligned. So that these axes are aligned, the off-centre top (31) of the convex surface (30) of the core (3) must be in the axis of the centres of the plates and therefore of the core (3) that being off centre in relation to the lower plate (2). Thus the rest position of the core (3) will be off centre in relation to the centre of the prosthesis. As illustrated in FIG. 3C, in which the upper plate (1) is not shown for reasons of clarity, the core is off centre in relation to the centre of the prosthesis and the co-operation means (33) of the core (3) are in contact with the co-operation means (23) of the lower plate (2), in the zones encircled with a dotted line. FIG. 2B also emphasises this shift of the core (3) in relation to the side view of the centre of the prosthesis. The shifting of the core (3) and the contact between the co-operation means (33) and those of the lower plate (23) will also restrict the displacement of the core (3) in the opposite direction to that of the off centre of the top (31) of the convex surface (30). We can then choose the direction and amplitude of the shift to be made to the top (31) of the convex surface (30) of the core (3), in order to obtain a desired reduction in displacement. The core (3) can then, for example, only be displaced in the direction of the shifting of the top (31) in relation to the centre (32) of the convex surface (30) of the core (3). If the patient wearing the prosthesis according to this embodiment bends over in the opposite direction to this shifting of the top (31), the core (3) can then move in the direction of this shifting of the top (31), thus reducing the shifting between the vertical axes passing through the centres of the plates, which is what would happen if the top (31) of the convex surface (30) of the core (3) was not off centre. An essential consequence of this feature is therefore that it allows to permanently restrict the shifting between the vertical axes passing through the centres of the vertebrae, even when the patient bends over. For example, we can choose a core (3) whose top (31) of its convex surface (30) is off centre to the rear so that the core, in the rest position, is completely off centre to the front of the prosthesis and can not be displaced further forward. Such a core therefore restricts the displacement of the core to the front and reduces the angle to which the patient can bend backwards. However, if the patient bends forward, the upper plate (1) inclines to the front, thus inducing a shifting of the vertical axis passing through its centre, in relation to the vertical axis passing through the centre of the lower plate (2). However, this shifting is eliminated by displacing the core (3) to the rear of the prosthesis. This shifting is better eliminated when the upper plate is mobile about the off-centre top (31) of the convex surface (30) of the core (3). The core (3) with an off-centre top (31) then wedges into the rear of its opening in the prosthesis and allows a better alignment of the vertical axes passing through the centres of the plates than a core with an off-centre top does.

Another advantage of some embodiments relates to the implanting of prostheses between the vertebrae of a recipient patient. During implantation of prostheses with mobile cores, the core of the prosthesis has a tendency to move to a far end of its stroke in its opening within the prosthesis. The patient is thus equipped with a prosthesis which imposes a slight inclination to his/her spinal column. This inclination can be eliminated thanks to the movements of the patient as soon as he/she has recovered from the operation. However, this inclination provokes considerable discomfort for the patient. Thanks to the off-centre position of the top (31) of the core (3) of the prosthesis according to preferred embodiments, the core (3) would tend to move into an off-centre rest position, in which the top (31) is aligned in relation to the axes of the upper and lower plates. Thanks to this spontaneous alignment of the axes of the prosthesis, no inclination of the plates will be imposed in the rest position and the patient will have been equipped with a prosthesis that does not provoke any discomfort.

Figure 1B:
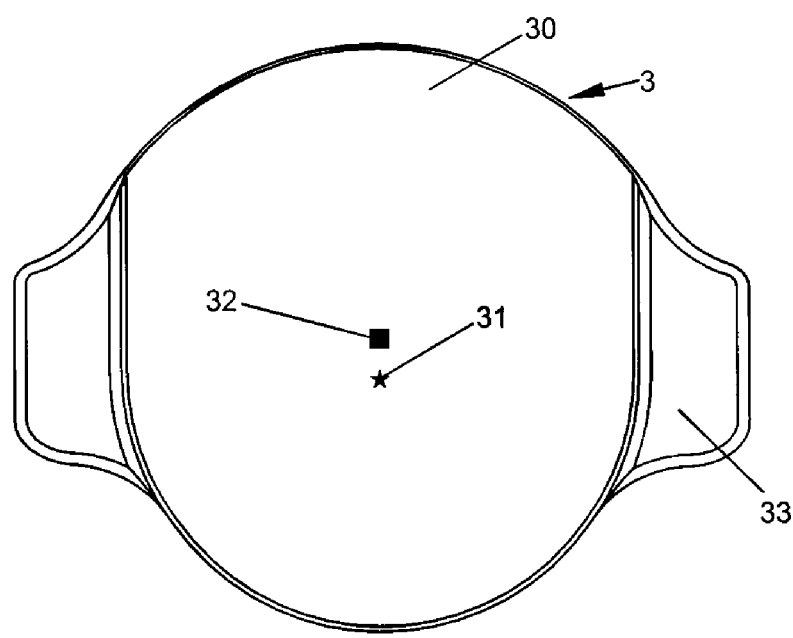

In the embodiment in FIGS. 1 to 3, the core (3) has male co-operation means (33) complementary with female co-operation means (23) present on the lower plate (2). The male co-operation means (33) of the core (3) are, for example, hasps substantially parallelepiped in shape, as particularly visible in FIGS. 1a and 1b. The female co-operation means (23) can, as particularly visible in FIGS. 3a and 3b, consist, for example, in four walls situated, in pairs, on each of the two side edges of the lower plate (2). These walls could be curved toward the centre of the prosthesis, so as to cover at least a part of the male co-operation means (33) of the core (3) and avoid lifting the core (3) and the upper plate (1). In this embodiment illustrated in FIGS. 1 to 3, the dimensions of each male means (33) of the core (3) are slightly less than those of each female means (22) of the lower plate (2), so as to allow a restricted clearance of the core (3) in relation to the lower plate (2), both in translation according to an axis substantially parallel to the lower plate (2), and in rotation about an axis substantially perpendicular to the lower plate (2). These co-operation means (23, 33) also prevent the core (3) from ejecting out of the prosthesis, in the event of too much constraint on the prosthesis.

In an alternative embodiment not shown, the dimensions of each male co-operation means (33) of the core (3) are substantially the same as those of each female co-operation means (23) of the lower plate (2), so as to avoid any clearance of the core (3) in relation to the lower plate (2), both in translation and in rotation. In the latter case, the only permitted movement of the prosthesis is that of the upper plate (1) in relation to the core (3).

In an alternative embodiment not shown, the core (3) has female co-operation means, consisting, for example, in complementary recesses of the male means present on the lower plate (2). These male means of the lower plate (2) can consist, for example, in two contact plates or two nibs, for example curved toward the interior of the prosthesis and facing one another on two edges of the lower plate (2).

In another alternative embodiment not shown, the lower plate (2) has dowels. The core (3), by way of complement, has two wells under its lower surface. The dimensions of the dowels of the lower plate (2) and of the wells of the core (3) will be adapted according to the desired result, by choice, of slight clearance of the core in translation and in rotation or any clearance.

In an alternative embodiment not shown, a part of the upper surface of the upper plate (1) is bulged, so as to better adapt to the vertebra on which the prosthesis is intended to be placed, the lower surface of the vertebrae being hollow. The bulged part of the upper plate (1) is then situated in the front part of the upper plate. The lower plate (2) is substantially plane as its lower surface has no need to be bulged or hollow, since the upper surface of the vertebrae is substantially flat.

It must be evident for specialists that the invention allows embodiments in numerous other specific forms without departing from the scope of application of the invention as claimed. As a consequence, the embodiments must be considered by way of illustration, but can be modified within the scope defined by the range of the attached claims, and the invention does not have to be limited to the details given above.

The invention claimed is:

1. An intervertebral disc prosthesis the prosthesis comprising:
   an upper plate comprising an upper vertebral contact surface;
   a lower plate comprising a lower vertebral contact surface;
   a core having a length and a transverse width between opposite lateral edges, the core comprising
      a body comprising a lower generally planar sliding surface disposed on one side of the body, and an upper convex sliding surface disposed on an opposite side of the body and having a length and a transverse width, with the length of the upper convex sliding surface being greater than its width,
      a first tab extending from the body along one edge of the core, the first tab having a width less than the length of the core, and
      a second tab extending from the body along an opposite edge of the core, the second tab having a width less than the length of the core;
   a lower core-facing surface disposed on the upper plate on a side opposite the upper vertebral contact surface, the lower core-facing surface comprising a protrusion bearing a concave sliding surface having a length that is less that the length of the upper convex sliding surface;
   an upper core-facing surface disposed on the lower plate on a side opposite the lower vertebral contact surface, the upper core-facing surface comprising a generally planar upper sliding surface that is sized to permit translational movement of the core in the direction of its length and the direction of its width and rotation of the core about an axis perpendicular to the generally planar upper sliding surface;
   a first pair of protrusions extending from the upper core-facing surface proximal to a first edge of the lower plate, the first pair of protrusions spaced apart a distance greater than the width of the first tab; and
   a second pair of protrusions extending from the upper core-facing surface proximal to a second edge of the lower plate on the opposite side of the lower plate from the first edge of the lower plate, the second pair of protrusions spaced apart a distance greater than the width of the second tab.

2. The intervertebral disc prosthesis of claim 1 in which each of the protrusions comprises an incurvate wall.

3. The intervertebral disc prosthesis of claim 2 in which each of the protrusions comprises a recess sized to movably house a portion of one of the first or second tabs.

4. An intervertebral disc prosthesis comprising
   an upper plate having a curved lower surface;
   a core rotatable with respect to the upper plate along a curved upper surface of the core that has length greater that its width, the core comprising
      a flat core surface disposed on a side of the core opposite the curved upper surface,
      a perimeter wall extending around the edge of the core between the curved upper surface and the flat core surface, the wall having a first height at a first end of the length of the curved upper surface and a second height at a second end of the length of the curved upper surface opposite the first end, with the first height greater than the second height and each of the first and second heights being less than a third height of the core located at a point of the core located within the perimeter wall, and
      plural lugs projecting away from the perimeter wall along opposite sides of the core; and
   a lower plate translatable and rotatable with respect to the core along a flat plate surface in slidable engagement with the flat core surface, the lower plate further comprising plural pillars disposed on opposite edges of the lower plate, with each of the pillars having a recess sized to loosely accept a portion of one of the plural lugs.

5. The intervertebral disc prosthesis of claim 4 in which the lugs have a generally parallelepiped shape.

6. The intervertebral disc prosthesis of claim 5 comprising two pairs of pillars, with the pairs disposed on opposite edges of the lower plate and each of the recesses sized to loosely accept a separate corner of the lugs.

* * * * *